United States Patent [19]

Zaiger et al.

[11] Patent Number: Plant 6,472

[45] Date of Patent: Dec. 20, 1988

[54] PEACH TREE ("AMPARO")

[76] Inventors: Chris F. Zaiger, 537 Rosemore Ave.; Gary N. Zaiger, 1907 Elm Ave.; Leith M. Gardner, 1207 Grimes Ave.; Grant G. Zaiger, 2121 Elm Ave., all of Modesto, Calif. 95351

[21] Appl. No.: 37,639

[22] Filed: Apr. 13, 1987

[51] Int. Cl.[4] ..... A01H 5/03

[52] U.S. Cl. ..... Plt./43

[58] Field of Search ..... Plt./43

*Primary Examiner*—Robert E. Bagwill

[57] ABSTRACT

A new and distinct variety of peach tree which has the following unique combination of desirable features:

1. Vigorous upright growth.
2. Heavy and regular bearer of yellow flesh, freestone fruit.
3. Fruit being large and nearly uniform in size throughout the tree.
4. The fruit having very firm flesh with very good storage and shipping quality.
5. Fruit holding firm on tree for 7–10 days after shipping ripe.
6. Fruit with good flavor and eating quality.
7. Fruit having a high degree of attractive red skin color.

1 Drawing Sheet

ORIGIN OF THE VARIETY

The present new and distinct variety of peach tree was originated by us in the experimental orchard, located at Modesto, Calif. as a first generation seedling of a cross between two seedling selections. The maternal seedling parent was a selection from a group of open-pollinated O'Henry Peach (U.S. Plant Pat. No. 2,964) seedlings and the pollen-parent originated from a cross between two seedling selections; one seedling (the maternal parent) originated from a group of open-pollinated May Grand Nectarine (U.S. Plant Pat. No. 2,794) seedlings and the pollen-parent originated from seedlings of open-pollinated Sam Houston Peach (Non-patented).

ASEXUAL REPRODUCTION OF THE VARIETY

Our new and distinct variety of peach tree was asexually reproduced by budding in the experimental orchard located at Modesto, Calif., and the reproductions show that said characteristics of the tree and its fruit are established and transmitted through succeeding reproductions and come true to the original tree in all respects.

SUMMARY OF THE VARIETY

The new and distinct variety of peach tree which is of large size, medium dense, upright in growth and a regular and productive bearer of large, very firm, yellow flesh, freestone fruit with good flavor and eating quality. The present variety of peach tree is further characterized as to its novelty by producing fruit that will hold firm on the tree 7–10 days after shipping ripe, being nearly uniform in size throughout the tree, having very good storage and shipping quality and having a high degree of attractive red skin color.

DESCRIPTION OF THE PHOTOGRAPHS

The accompanying color photographs show typical specimens of the foliage and fruit of the present new variety of peach tree, with the exterior and cross sectional view of the fruit divided in its suture plane to reveal flesh coloration, pit cavity and showing a stone remaining in place. The photographs were taken shortly after being picked at maturity (shipping ripe) and the colors are as nearly true as is reasonable possible in a color representation of this type.

DESCRIPTION OF THE VARIETY

The following is a detailed botanical description of the new variety of peach tree, its foliage, flowers and fruit as based on observations of specimens grown at Modesto, Calif., with color terminology (except those in common terms) in accordance with Reinhold Color Atlas by A. Korneruf and J. H. Wanscher.

Tree:
- *Size.*—Large.
- *Vigor.*—Vigorous.
- *Growth.*—Upright.
- *Density.*—Medium dense.
- *Bearer.*—Regular.
- *Production.*—Productive.

Trunk:
- *Size.*—Medium to large.
- *Surface.*—Medium shaggy.
- *Color.*—Brown to grayish brown.

Branches:
- *Size.*—Medium stocky.
- *Surface.*—Smooth to medium rough.
- *Lenticels.*—Numerous. Medium size.
- *Color.*—Brown to grayish brown.

Leaves:
- *Size.*—Large. Average length — 7". Average width — $1\frac{5}{8}$".
- *Texture.*—Smooth.
- *Margin.*—Crenate.
- *Form.*—Lanceolate. Pointed.
- *Thickness.*—Medium.
- *Petiole.*—Medium length. Medium thickness.
- *Glands.*—Reniform. Number varies from 2 to 6. Average number 3. Located on base of leaf and upper portion of petiole.
- *Color.*—Upper surface — green (27-E-8) to dark green (27-F-8). Lower surface — grayish green (27-E-4) to dull green (27-E-5).

Flower buds:
- *Size.*—Large.

*Length.*—Medium.
*Pubescence.*—Pubescent.

Flowers:
*Blooming period.*—Mar. 1, 1985 to Mar. 7, 1985. Varies slightly due to climatic variations.
*Size.*—Large — showy.
*Color.*—Pink.
*Pollen.*—Present.

Fruit:
*Maturity when described.*—Hard ripe.
*Date of first picking.*—June 23, 1985.
*Date of last picking.*—June 30, 1985.
*Size.*—Large. Average diameter axially — 2 15/16 ". Average tranversely in suture plane — 3".
*Form.*—Nearly globose, some fruit slightly larger on one side and slightly more retuse at the base.
*Suture.*—Shallow — extends from base to apex, some fruit with slight depressions in suture line.
*Ventral surface.*—Usually rounded, varies from equal to unequal.
*Apex.*—Varies from rounded to slight pistol point.
*Base.*—Retuse.
*Cavity.*—Moderately rounded to elongated in suture plane. Average depth — ½". Average breadth — ¾".

Flesh:
*Texture.*—Very firm.
*Fibers.*—Moderate number, tender.
*Juice.*—Moderate.
*Amygdlin.*—Undetected.
*Ripens.*—Evenly.
*Flavor.*—Mild.
*Aroma.*—Moderate.
*Eating quality.*—Good.
*Color.*—Golden yellow (5-A-5) to (5-A-7). Stone Cavity — orange red (8-B-7) to (8-B-8) very slight bleeding of orange red into flesh from pit cavity.

Skin:
*Thickness.*—Medium.
*Texture.*—Medium. Tenacious to flesh.

*Tendency to crack.*—None — small indentation on suture line.
*Down.*—Moderate. Medium length.
*Color.*—Yellow ground color (4-A-6) to (4-A-8) overspread with red (9-B-7) to (9-C-8).

Stone:
*Type.*—Freestone — flesh adheres to some small pit cavities.
*Size.*—Large. Average length — 1 7/16". Average width — 1 ⅛". Average breadth — ¾".
*Form.*—Ovid.
*Sides.*—Mostly equal — some unequal.
*Apex.*—Acuminate.
*Base.*—Usually rounded — some straight.
*Surface.*—Irregularly furrowed toward apex and pitted toward base.
*Ridges.*—Rounded.
*Tendency to split.*—Very slight.
*Color.*—Reddish brown (8-D-6) to mahogany brown (8-D-7).

Use: Dessert.
*Market.*—Local and long distance.
Keeping quality: Very good.
Shipping quality: Very good.

The new and distinct variety of peach tree and its fruit may vary in slight detail due to climatic, soil and cultural practices under which the variety may be grown; the present description being that of the new variety grown under the ecological conditions prevailing at Modesto, Calif.

The following is claimed:

1. A new and distinct variety of peach tree, as illustrated and described, characterized by its large size, vigorous, upright growth and a productive and regular bearer of very firm, yellow flesh, freestone fruit with good flavor and eating quality; the fruit is further characterized by being nearly uniform in size throughout the tree, holding firm on the tree for 7–10 days after shipping ripe, having very good shipping and storage quality and having a high degree of attractive red skin color.

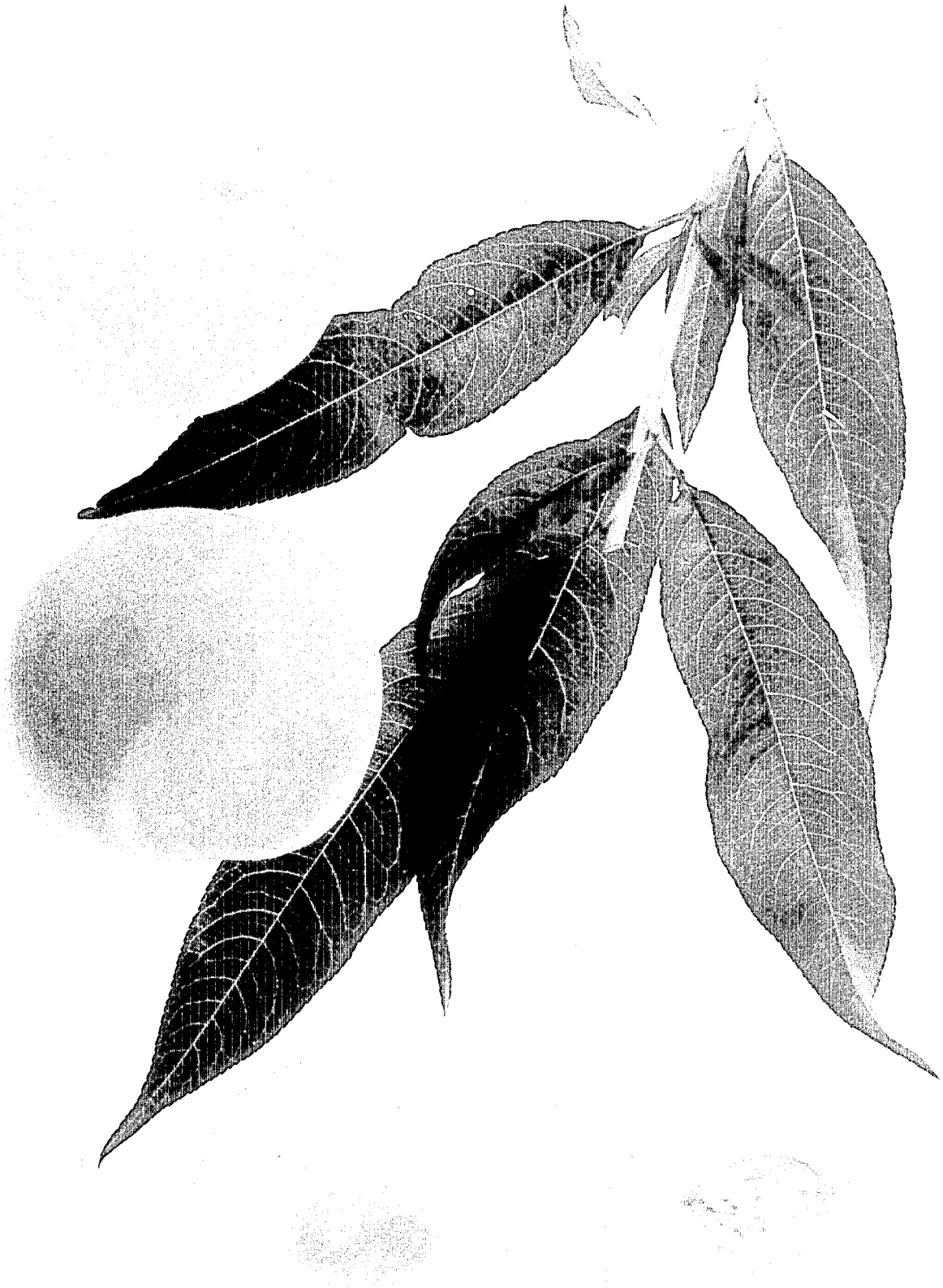

* * * * *